United States Patent [19]

Honda et al.

[11] 4,439,197
[45] Mar. 27, 1984

[54] MEDICAL CAPSULE DEVICE

[75] Inventors: Mikio Honda; Koichi Matsui; Kitijiro Kohri; Kazuo Misawa; Koji Kambara, all of Tokyo, Japan

[73] Assignee: Olympus Optical Co., Ltd., Tokyo, Japan

[21] Appl. No.: 358,112

[22] Filed: Mar. 15, 1982

[30] Foreign Application Priority Data

Mar. 23, 1981 [JP] Japan .................................. 56-41878

[51] Int. Cl.³ ............................................. A61M 7/00
[52] U.S. Cl. ................... 604/891; 128/769; 128/655; 604/890
[58] Field of Search ............... 128/213 R, 214 F, 760, 128/769, DIG. 12, 631, 655; 604/890, 891, 48, 93, 131, 134, 5

[56] References Cited

U.S. PATENT DOCUMENTS 3,485,235 12/1969 Felson ....................... 128/2
3,606,592 9/1971 Mudurski et al. .......... 3/1.7 X
4,360,019 11/1982 Portner et al. ............. 604/891

FOREIGN PATENT DOCUMENTS 337989 6/1959 Switzerland ..................... 604/890

Primary Examiner—Edward M. Coven

[57] ABSTRACT

A medical capsule device includes a capsule body provided with a chamber inside and a communicating path for communicating the chamber with the outside, a movable member arranged in the chamber and movable between a liquid-pushing position at which the volume of the chamber is made smallest and a liquid-receiving position at which the volume of the chamber is made largest, a coiled operating member made of a shape memory alloy for selectively moving the movable member to the liquid-receiving or -pushing position according to temperature changes of the operating member itself, and a switching circuit and power supply source arranged in the capsule body and adjusting the temperature of the operating member to selectively move the movable member to the liquid-pushing or -receiving position.

5 Claims, 5 Drawing Figures

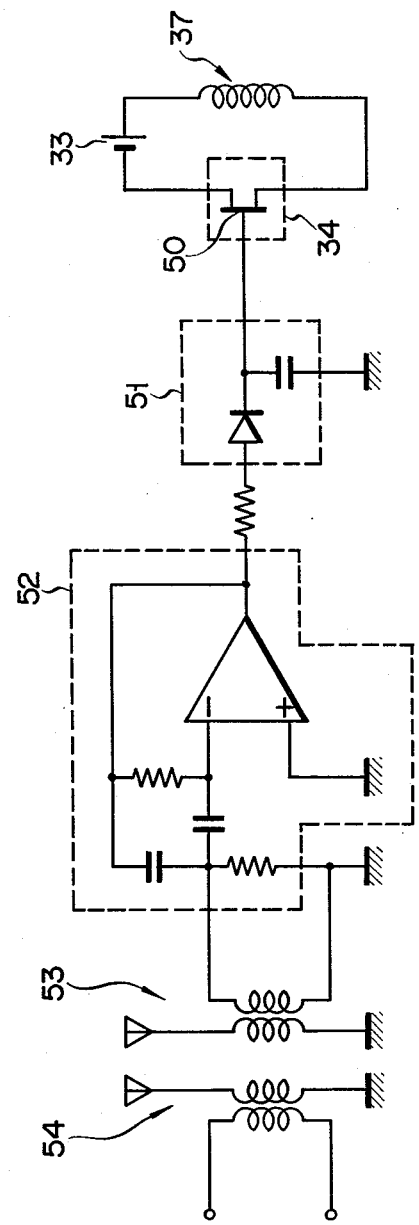
F I G. 5

MEDICAL CAPSULE DEVICE

BACKGROUND OF THE INVENTION

The present invention relates to a medical capsule device employed to spread a liquid medicine or to sample data such as body liquid in the body cavity.

The conventional medical capsule device of this type includes a chamber arranged in a capsule body so as to receive medical fluid or data, a movable member arranged freely reciprocatingly in the chamber, and a thread or digestive film for holding the movable member against the action of a spring at a position where medical fluid is contained or at a position where medical fluid contained is pushed out of the chamber. When the thread or digestive film is cut or dissolved, the movable member is moved by the action of spring to its pushed or withdrawn position to discharge medical fluid outside the chamber or to receive data in the chamber.

When the capsule is once used, however, the thread or digestive film for holding the movable member at its pushed or withdrawn position is cut or solved, thus making it impossible to once more use the used capsule. A troublesome work for disassembling and re-assembling the used capsule is therefore needed to use the a used capsule again, and the re-use of used capsule is thus made disadvantageous practically.

Another conventional medical capsule device includes a stopper for holding the movable member at its pushed or withdrawn position in the chamber against the action of a spring, and a ratchet for engaging with the stopper and turned by vibration applied from outside to release the stopper therefrom. However, this medical capsule device becomes so complicated in construction as to make it difficult to make the capsule small-sized and also needs the disassembling work in the case of re-use of a used capsule.

SUMMARY OF THE INVENTION

The object of the present invention is therefore to provide a medical capsule device enabling the used capsule to be re-used without disassembling it and simple in construction.

BRIEF DESCRIPTION OF THE DRAWINGS

FIGS. 1 and 2 are sectional views showing one embodiment of a medical capsule device according to the present invention, in which FIG. 1 shows a movable member held at its withdrawn position and FIG. 2 shows the movable member held at its pushed position;

FIGS. 3 and 4 are sectional views showing another embodiment of a medical capsule device according to the present invention, in which FIG. 3 shows the movable member held at its pushed position and FIG. 4 shows the movable member held at its withdrawn position; and FIG. 5 is a circuit diagram showing an example of a temperature adjustment mechanism.

DETAILED DESCRIPTION OF THE PREFERRED EMBODIMENTS

Figure 1:
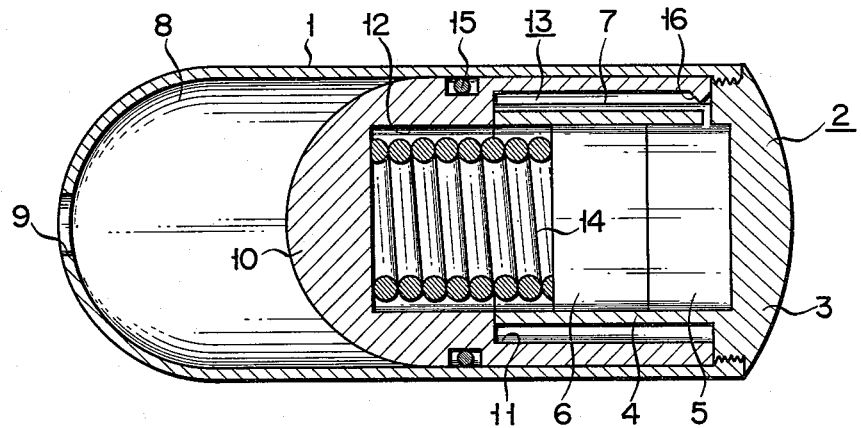
Figure 2:
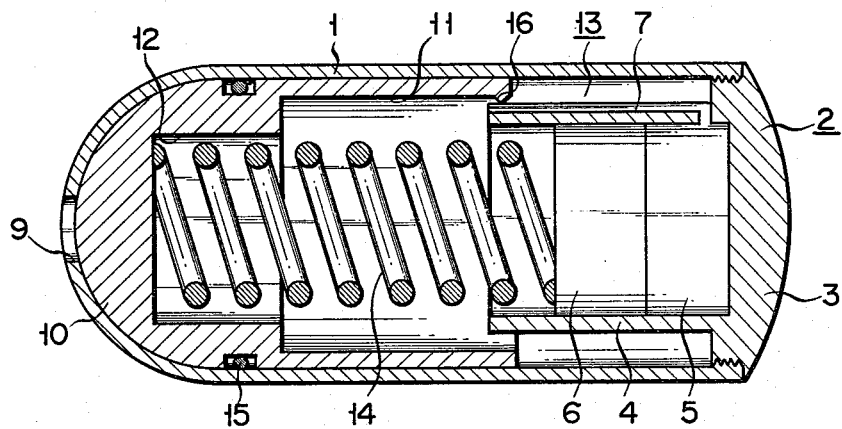

Embodiments of the present invention will be described with reference to the drawings. FIGS. 1 and 2 show an embodiment of the present invention, in which numeral 1 represents a bottomed cylindrical capsule body and 2 a holding member screwed into an opening of capsule body 1 to close it, both being made of insulating synthetic resin such as epoxy resin. The holding member 2 includes a cover 3 having a male thread portion engaged with a female thread portion formed on the inner circumferential wall of the opening of capsule body 1, and a cylindrical holding portion 4 formed integral with the cover 3 and coaxial with the capsule body 1, with its one end connected to the inner face it is of cover 3 while with its outer circumferential wall spaced from the inner circumferential wall of capsule body 1. A power supply source 5 and a switching circuit 6 on-off-controlled, as publicly well known, by electric wave signal applied from outside are housed in a space enclosed by the holding member 2. A piece of conductive contact 7 is attached to the outer circumference of holding member 2 and extends along the axial direction of holding portion 4. One end of this contact piece 7 is electrically connected to the power supply source 5.

A chamber 8 is provided before the holding member 2 in the capsule body 1 and communicated with outside through a through-hole 9 provided in the bottom of capsule body 1. The through-hole 9 has such a dimension (0.1 cm in diameter, for example) that prevents liquid such as medical fluid contained in the chamber 8 from being discharged outside the capsule body 1 through the through-hole 9 under usual conditions while liquid such as body liquid outside the capsule body 1 is presented from entering into the chamber 8 through the through-hole 9 under usual conditions. A bottomed cylindrical movable member 10 is arranged in the chamber 8 in such a way that it can be freely reciprocated along the inner wall of capsule body 1 from its liquid-receiving position to its liquid-pushing position and vice versa. This movable member 10 is made of conductive material such as stainless steel and provided with a circular hole 11 at its opened back end, said hole 11 having an outer diameter larger than that of holding portion 4 of holding member 2. The movable member 10 is also provided with another circular hole 12 formed coaxial and communicated with the circular hole 11, said circular hole 12 having the same inner diameter and the same length as those of holding portion 4 of holding member 2. A projection 16 always contacted with the contact piece 7 is formed on the inner circumferential wall of the opening of movable member 10. The movable member 10, contact piece 7 and power supply source 5 form a current flowing circuit 13, which is combined with the switching circuit 6 to form a temperature adjustment mechanism. The current flow circuit 13 is operationally connected to the switching circuit 6 according to the publicly well known technique in such a way that current is allowed to flow from the power supply source 5 to an operating member 14 when the switching circuit 13 is turned on but that current is not allowed to flow when turned off. The coiled operating member 14 is interposed between the bottom of circular hole 12 in the movable member 10 and switching circuit 6, with its one end attached to the bottom of circular hole 12 in the movable member 10 while with its other end it is connected to the switching circuit 6. This operating member 14 is made of a shape memory alloy consisting of Cu-Zn-Al alloy, for example, and this alloy has reversibility. The coiled operating member 14 is extended as shown in FIG. 2 when the crystalline structure of the shape memory alloy is under mother phase (or high temperature phase) while contracted as shown in FIG. 1 when under martensite phase (or low temperature phase). When the crystalline structure of the shape memory alloy of which the operating member 14 is made is under martensite phase, therefore, the movable member 10 is held at its liquid-containing position by the operating member 14 with its opened end urged against the cover 3 of holding member 2 as shown in FIG. 1, while when under mother phase, it is held at its liquid-pushing position by the operating member 14 with its foremost end (or bottom) urged onto the bottom of capsule body 1 as shown in FIG. 2. The operating member 14 is made of a shape memory alloy whose crystalline structure starts to reversely change from martensite to mother phase at a temperature higher than that of the human body, and consisting of copper (about 73%), zinc (about 20%) and aluminum (about 7%), for example. The whole surface of operating member 14 except its ends connected to the movable member 10 and switching circuit 6 is insulatingly coated with synthetic resin. Numeral 15 represents an O-ring arranged around the outer circumference of movable member 10 is fluid-tightly seal between the movable member 10 and capsule body 1.

In the case where the medical capsule device having such arrangement as described above is used to spread medical fluid in the body cavity, desired medical fluid is injected into the chamber 8 via the through-hole 9, previously holding the movable member 10 at its liquid-receiving position in the capsule body 1 as shown in FIG. 1. The capsule body 1 thus prepared is swallowed by a patient. Medical fluid fails to come outside through the through-hole 9 at this time due to its surface tension. When the capsule body 1 thus swallowed arrives at a predetermined position in the body cavity, the switching circuit 6 is turned on by electric wave signal applied from outside. When the switching circuit 6 is turned on, current is allowed to flow from the power supply source 5 to the operating member 14 through the contact piece 7 and movable member 10. When current flows to the operating member 14, the operating member 14 itself is heated thanks to electrical resistance. When the temperature of operating member 14 becomes higher than the temperature (As) at which it starts its reverse deformation, the crystal structure of the shape memory alloy of which the operating member 14 is made start to return from martensite to mother phase. When the temperature of operating member 14 reaches a finish temperature (Af), the operating member 14 finishes its reverse deformation and is deformed from its coil-contracted shape to its coil-extended shape. This deformation of operating member 14 causes the movable member 10 to move from its liquid-containing position (FIG. 1) to its liquid-pushing position (FIG. 2), so that medical fluid contained in the chamber 8 can be spread in the body cavity as the movable member 10 moves.

In the case where the medical capsule device is used to sample data, the switching circuit 6 is turned on, causing current to flow to the operating member 14 and the operating member 14 to be heated, so that the crystalline structure of shape memory alloy of which the operating member is made is changed to mother phase, that is, the operating member 14 is deformed to its coil-extended shape. The capsule body 1 in which the movable member 10 is held at its liquid-pushing position by this deformation of operating member 14 as shown in FIG. 2 is sent into the body cavity. When the capsule body 1 reaches a predetermined position, the switching circuit 6 is turned off by a command applied from outside. When the supply of current to the operating member 14 is stopped, the operating member 14 radiates heat and its temperature thus becomes low. The shape memory alloy of which the operating member 14 is made effects martensite transformation, thus causing the operating member 14 to be deformed from its coil-extended shape to its coil-contracted shape. This deformation of operating member 14 causes the movable member 10 to move from its liquid-pushing position (FIG. 2) to its liquid-receiving position (FIG. 1), so that data such as body liquid can be sampled from the predetermined position in the body cavity into the chamber 8 as the movable member 10 moves.

In the case of a medical capsule device having such arrangement as described above, the operating member 14 can be deformed to have predetermined forms by turning the switching circuit 6 on and off so that the movable member 10 may be moved to its liquid-receiving position shown in FIG. 1 or to its liquid-pushing position shown in FIG. 2. Therefore, the once-used capsule body 1 can be re-used without being conventionally disassembled. In addition, neither of the means for cutting the thread, dissolving the digestive film and ratchet means is not needed in the capsule body 1, thus enabling the capsule body 1 to be made simple in arrangement.

In the above-described embodiment, the operating member 14 is deformed to have its coil-extended form as shown in FIG. 2 when the crystalline structure of its alloy is under mother phase while to have its coil-contracted form as shown in FIG. 1 when under martensite phase. However, its coil may be contracted when under mother phase while extended when under martensite phase.

Figure 3:
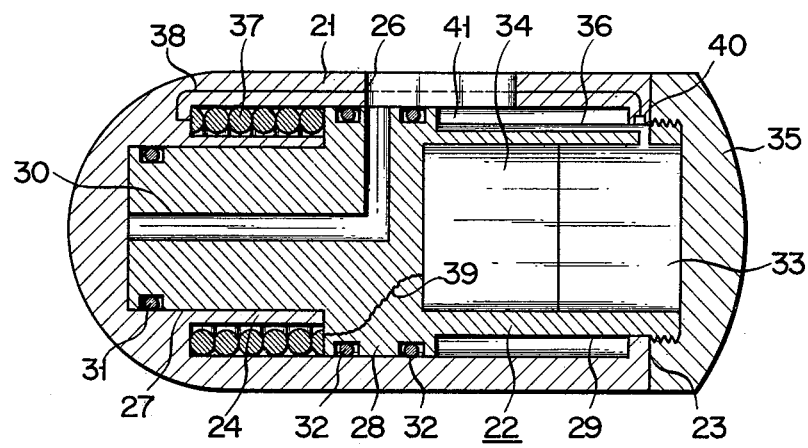
Figure 4:
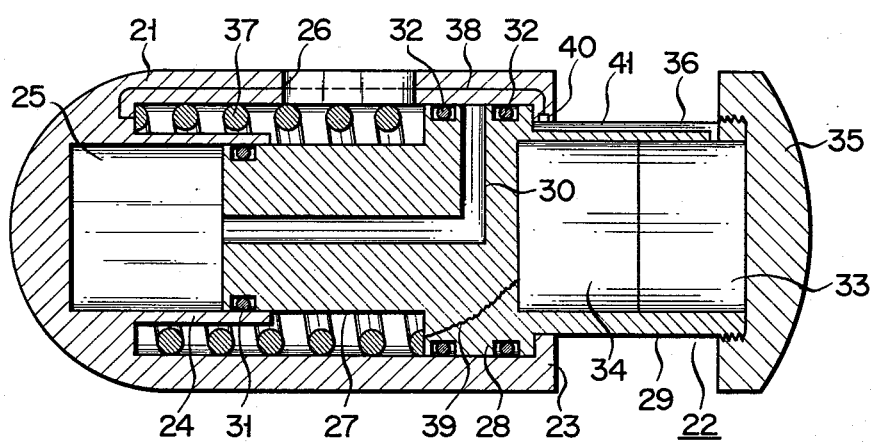

FIGS. 3 and 4 show another embodiment of the present invention by which the above-mentioned latter case is embodied. Numeral 21 denotes a bottomed cylindrical capsule body which is made of insulating material such as synthetic resin, and numeral 22 a movable member arranged in the capsule body 21 and reciprocating along the inner circumferential wall of capsule body 21 from its liquid-pushing position shown in FIG. 3 to its liquid-receiving position shown in FIG. 4. A ring-shaped stopper portion 23 is projected inwards from the inner circumferential wall at the opened end of capsule body 21. A cylindrical guide portion 24 is formed in the capsule body 21 and spaced from the outer circumferential wall extending from the bottom of capsule body 21 to the opened end thereof. A chamber 25 is formed inside the guide portion 24. A slot 26 extending in the axial direction of capsule body 21 is formed in the outer circumferential wall of capsule body 21.

The movable member 22 comprises a columnar piston portion 27 arranged freely reciprocatingly inside the guide portion 24 of capsule body 21 so as to change the volume of chamber 25 and having the smallest diameter, a columnar guide portion 28 projected from the back end face of piston portion 27 so as to slide along the inner circumferential face of capsule body 21 and having the largest diameter, and a cylindrical holding portion 29 projected from the back end face of guide portion 28 and having a middle diameter, these portions being made of insulating material and formed coaxially integral to one another. A communicating hole (or communicating path) 30 comprising a hole extending radially from the outer circumferential face of guide portion 28 and a hole extending axially from the foremost end face of piston portion 27 to communicate with the closed end of radially-formed hole is formed in the movable member 22. The opened end of the radially-formed hole of this communicating path 30 is closed by the circumferential wall of capsule body 21 when the movable member 22 is in its liquid-receiving position as shown in FIG. 4, but communicated with the outside through the slot 26 in the circumferential wall of capsule body 21 when the movable member 22 is in the other positions except its liquid-receiving position. An O-ring 31 is arranged around the outer circumference at the foremost end of piston portion 27 and a pair of O-rings 32 are also arranged on both sides of the opened end of communicating path 30 and around the outer circumference of guide portion 28. A power supply source 33 and a switching circuit 34 are housed, similarly to the first embodiment, in a space defined by the inner circumference of holding portion 29, and a cover 35 is threaded onto the opened end of this holding portion 29 to close the space. The power supply source 33 can be exchanged with a new one when the cover 35 is detached. A piece of conductive contact 36 extending in the axial direction of holding portion 29 is arranged on the outer circumference of holding portion 29, with its one end connected to the power supply source 33.

A coiled operating member 37 is arranged in the capsule body 21, with its one end attached to the bottom of capsule body 21 while with its other end it is attached to the circumferential edge of the front face of guide portion 28 of movable member 22, and the whole surface of operating member 37 is insulatingly coated except these both ends thereof. The operating member 37 is made of a shape memory alloy and deformed to have its coil-contracted form when the crystalline structure of the shape memory alloy is under mother phase (or high temperature phase) while to have its coil-extending form as shown in FIG. 4 when under martensite phase (or low temperature phase). Therefore, when the crystalline structure of the shape memory alloy of which the operating member 37 is made is under martensite phase, the movable member 22 is held at its liquid-receiving position by the operating member 37, as shown in FIG. 4, urging the guide portion 28 against the stopper portion 23 of capsule body 21, while when under mother phase, it is held at its liquid-pushing position, as shown in FIG. 3, urging its foremost end onto the inner face of the bottom of capsule body 21. The shape memory alloy of which the operating member 37 is made starts to return from martensite to mother phase at the temperature (As) higher than the body temperature, and consists of copper (about 73%), zinc (about 20%) and aluminum (about 7%), for example.

One end of operating member 37 is electrically connected to one end of a lead line 38 embedded in the capsule body 21 while the other end thereof is connected to one end of a lead line 39 embedded in the movable member 22. The other end of lead line 38 is electrically connected to a contact 40, which is arranged at the foremost end of stopper portion 23 to slide on the contact piece 36. The other end of lead line 39 is connected to the switching circuit 34. The power supply source 33, contact piece 36, contact 40 and lead lines 38, 39 are combined to form a current flowing circuit 41, which is combined with the switching circuit 34 to form the same temperature adjustment mechanism as that in the first embodiment.

An example of a temperature adjustment mechanism or electric circuit will be described referring to FIG. 5.

The switching circuit 34 for electrically connecting and disconnecting the operating member 37 to and from the power supply source 33 has an FET 50. The gate of FET 50 is connected to the output terminal of a rectifier circuit 51, whose input terminal is connected through a connection (not shown) to the output terminal of a band-pass filter 52 connected to the power supply source 33. A receiver 53 is connected to the input terminal of band-pass filter 52.

When an electric wave having a predetermined frequency is transmitted from an oscillator 54, it is received by the receiver 53. This signal received is fed through the band-pass filter 52 to the rectifier circuit 51, where it is rectified and then sent to the gate of FET 50 to turn on the switching circuit 34. As a result, the operating member 37 is heated by the power supply source 33. If the receiver 53 receives noise or a signal having a frequency except the predetermined one, the transmission of this noise or signal to the rectifier circuit 52 is stopped by the band-pass filter 52, thus preventing the switching circuit 34 from being turned on by this noise or signal.

In the case where the capsule device having such arrangement as described above is used to sample data in the body cavity, the switching circuit 34 is turned on to flow current to the operating member 37 and to cause the operating member to become heated due to its electrical resistance, thus holding the crystalline structure of shape memory alloy under mother phase. The movable member 22 is held at this time at its liquid-pushing position by the operating member 37 as shown in FIG. 3. The capsule body 21 thus previously prepared is inserted into the body cavity. When the capsule body 21 reaches a predetermined position in the body cavity, the switching circuit 34 is turned off by a command applied from outside. Current supply to the operating member 37 is thus stopped and the operating member 37 becomes low in temperature due to its natural radiation. Therefore, transformation to martensite phase is effected, so that the operating member 37 is deformed to change from its coil-contracted form to its coil-extended form. The movable member 22 is moved at this time by this deformation of operating member 37 from its liquid-pushing position (FIG. 3) to its liquid-receiving position (FIG. 4), thus enabling body liquid in the body cavity to be sampled into the chamber 25 through the slot 26 and communicating path 30 as the movable member 22 moves.

On the other hand, the switching circuit 34 is turned off to hold the crystalline structure of operating member 37 under martensite phase, and medical fluid or the like is injected into the chamber. The capsule body 21 thus previously prepared is inserted into the body cavity. When the capsule body 21 reaches a predetermined position in the body cavity, the switching circuit 34 is turned on to flow current to the operating member 37, which is thus heated due to its electrical resistance, causing the crystalline structure of the shape memory alloy, of which the operating member 37 is made, to effect reverse transformation from martensite to mother phase. Therefore, the operating member 37 is deformed to have its coil-contracted form as shown in FIG. 3, and the movable member 22 is moved by this deformation of operating member 37, thus enabling medical fluid in the chamber 25 to be spread in the body cavity through the communicating path 30 and slot 26 of capsule body 21.

As apparent from the above, the second embodiment can also achieve the same effects as those attained by the first embodiment.

It should be understood that the present invention is not limited to above-described embodiments. The operating member 37 may be made of any of shape memory alloys belonging to groups of Ti-Ni, Cu-Zn and Ni-Al, for example. It should also be understood that various changes and modifications can be made without departing from the spirit and scope of the present invention.

According to the present invention as described above, the medical capsule device is arranged in such a way that the movable member is reciprocated to the liquid-pushing or -receiving position in the chamber formed in the capsule body and communicated with the outside through the communicating path to change the volume of chamber, that the operating member is deformed according to its temperature changes to reciprocate the movable member, and that one of liquid-pushing and -receiving positions can be selected by the temperature adjustment mechanism. Therefore, when the operating member is adjusted in temperature by the temperature adjustment mechanism and deformed to have an appropriate form, the movable member can be moved from its liquid-pushing position to its liquid-receiving position. Accordingly, the medical capsule device of the present invention enables the once-used capsule body to be re-used without being disassembled and also the arrangement in the capsule body to be made simpler.

In addition, the operating member made of a shape memory alloy enables the shift amount of movable member to be made relatively larger to enhance the reliability of operation.

Further, the coiled operating member enables the space in the cylindrical capsule body to be effectively used and the work of arranging this operating member in the capsule body to be made easier.

Furthermore, the temperature adjustment mechanism comprising the current flowing circuit and switching circuit enables the medical capsule device to be made simpler in arrangement and smaller in size, as compared with the one wherein the fluid supply mechanism for supplying heating fluid to heat the operating member must be incorporated in the capsule body.

What we claim is:

1. A medical capsule device comprising:
   a capsule body provided with a chamber inside and a communicating path for communicating the chamber with the outside;
   a movable member arranged in the chamber and movable between a liquid-pushing position at which the volume of said chamber is made smallest and a liquid-receiving position at which the volume of said chamber is made largest;
   a coiled operating member made of a shape memory alloy whose crystalline structure shows martensite or mother phase according to changes of its temperature for selectively moving the movable member to the liquid-receiving or liquid-pushing position according to temperature changes of said operating member itself; and
   a temperature adjustment mechanism arranged in the capsule body including a power supply source electrically connected to the operating member, and a switching circuit connected between the power supply source and the operating member and capable of being remotely operated to start or stop the flow of current from the power supply source to the operating member, said temperature adjustment mechanism adjusting the temperature of said operating member to selectively move the movable member to the liquid-pushing or liquid-receiving position.

2. A medical capsule device according to claim 1, wherein said operating member contracts under mother phase causing the movable member to be moved to the liquid-pushing position and extends under martensite phase causing the movable member to be moved to the liquid-receiving position.

3. A medical capsule device according to claim 2 wherein said capsule body has a cylindrical form provided with an opened end, a closed end, and a circumferential wall in which a slot is formed extending in the axial direction of said capsule body, said movable member has an end facing the opened end of said capsule body and provided with a space formed therein, and another end facing the closed end of said capsule body to define the chamber therebetween, said movable member being slidable in the axial direction of said cylindrically-formed capsule body, said communicating path is formed in the movable member so as to communicate the chamber with the slot, and said temperature adjustment mechanism is arranged in the space.

4. A medical capsule device according to claim 1 wherein said operating member contracts under martensite phase causing the movable member to be moved to the liquid-receiving position and extends under mother phase causing the movable member to be moved to the liquid-pushing position.

5. A medical capsule device according to claim 4 wherein said capsule body has a cylindrical form provided with an opened end and a closed end in which the communicating path is partially formed, said movable member has an end facing the opened end of said capsule body and provided with a space formed therein, and another end facing the closed end of said capsule body to define the chamber therebetween, said movable member being movable in the axial direction of said cylindrically-formed capsule body, and said operating member is housed in the space.

* * * * *